United States Patent [19]

Paxson et al.

[11] 4,371,716
[45] Feb. 1, 1983

[54] β-(SEC-ALKOXY) ETHANOL PROCESS

[75] Inventors: Timm E. Paxson; Leo Kim, both of Houston, Tex.; Andre B. Van Aken, Amsterdam, Netherlands

[73] Assignee: Shell Oil Company, Houston, Tex.

[21] Appl. No.: 284,267

[22] Filed: Jul. 17, 1981

Related U.S. Application Data

[63] Continuation of Ser. No. 71,895, Sep. 4, 1979, abandoned.

[51] Int. Cl.$^3$ ............................................. C07C 41/06
[52] U.S. Cl. ..................................... 568/678; 568/697
[58] Field of Search ........................ 568/679, 697, 678

[56] References Cited

U.S. PATENT DOCUMENTS

| | | | |
|---|---|---|---|
| 2,067,385 | 1/1937 | Evans et al. | 568/697 |
| 4,139,566 | 2/1979 | Kim et al. | 568/679 |

FOREIGN PATENT DOCUMENTS

| | | | |
|---|---|---|---|
| 111296 | 12/1964 | Netherlands | 568/697 |
| 6401246 | 8/1965 | Netherlands | 568/678 |

*Primary Examiner*—Bernard Helfin

[57] ABSTRACT

An improved process for preparing β-(sec-alkoxy) ethanol which comprises reacting an olefin with ethylene glycol in the presence of a sulfuric acid or benzenesulfonic acid catalyst and sufficient sulfolane or alkyl-substituted sulfolane solvent to provide a one phase reaction medium, extracting the reaction products with an alkane and recovering the β-(sec-alkoxy) ethanol product from the alkane extract.

2 Claims, 3 Drawing Figures

FIG. 3
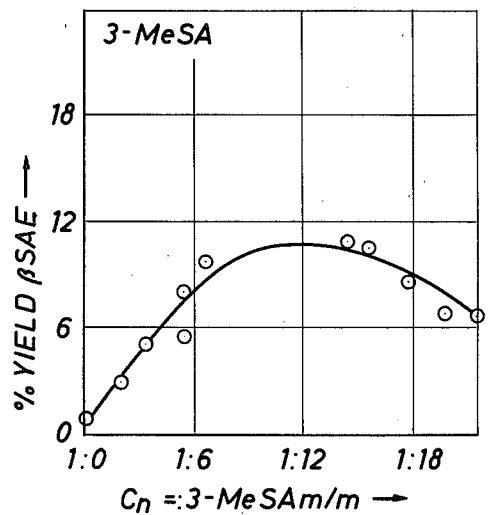
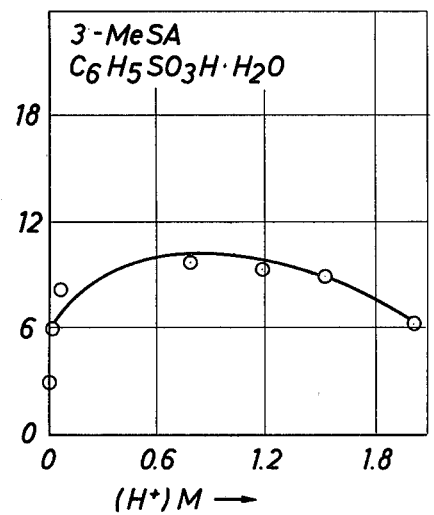
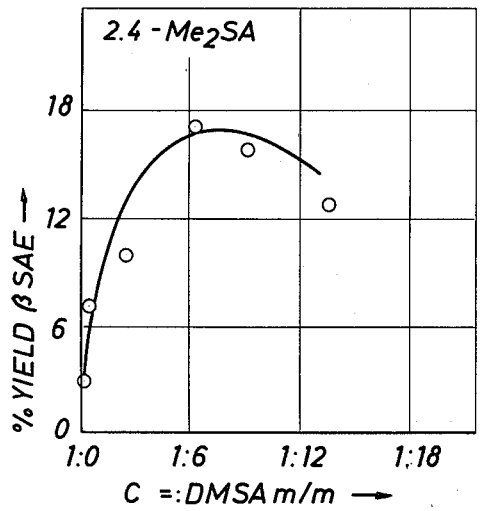
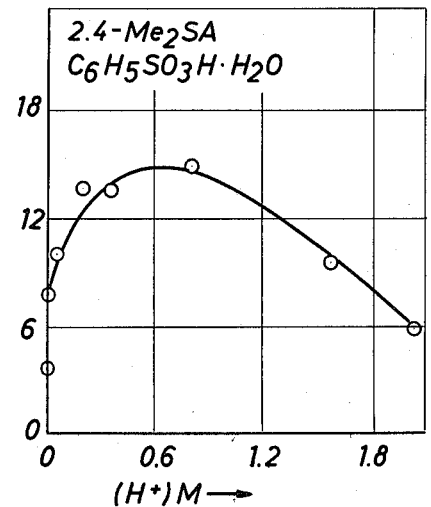

β-(SEC-ALKOXY) ETHANOL PROCESS

This is a continuation of application Ser. No. 071,895, filed Sept. 4, 1979 and now abandoned.

BACKGROUND OF THE INVENTION

1. Field of the Invention

This invention relates to a process for producing β-(sec-alkoxy) ethanol of the general formula $R_1R_2CHOCH_2CH_2OH$ from olefins and glycol.

2. Background of the Invention

Secondary alcohol ethoxylates are used as industrial detergents. A precursor of the secondary alcohol ethoxylate is β-(sec-alkoxy) ethanol from which the sec-alcohol ethoxylate can be made by conventional base catalyzed ethoxylation.

U.S. Pat. No. 2,067,385 issued Jan. 12, 1977, to Evans et al discloses the reaction of olefins with alcohols in the presence of strong acid catalysts such as sulfuric acid and benzene sulfonic acids. No particular effects of solvents are noted.

Netherlands Pat. No. 111,292 discloses the reaction of olefins with polyhydroxy compounds in the presence of acid catalysts such as $BF_3$, sulfuric acid, and aromatic sulfonic acids. The use of a polar solvent is disclosed such as sulfolane. No particular effects of one phase operation are noted.

The use of sufficient sulfolane type solvent to provide the phase operation provides enhanced rates of conversion. One phase operation, however, requires the use of relatively large amounts of solvent which must be removed from the product. Traditional methods for removing the sulfolane type solvents are impractical or extract tremendous economic penalties. The high boiling point of the sulfolane-type solvents (280° C. for sulfolane) can result in product decomposition if distillation is utilized especially over long time periods. Cooling the solvent-containing product to obtain phase separation is possible, but because of the larger amount of solvent used, a large heat cycle is involved which would extract a large economic penalty. Alternatively, water could be added to the cooled product mixture to enhance partitioning. But here an economic disadvantage arises from the need to cool and the need to remove the added water from the recycle stream. On the other hand, the use of a small amount of a paraffinic type solvent allows for high product recoveries at the same temperature as the reaction operates, thus minimizing heat load and product decomposition.

SUMMARY OF THE INVENTION

This invention provides a process for producing β-(sec-alkoxy) ethanols economically and in high yield. Rates are maximized and heat loads are minimized by the combined use of a one phase reaction solvent and an alkane extraction solvent. Basically, the process comprises reacting a $C_8$-$C_{22}$ olefin with ethylene glycol at 80° C. to 180° C. in the presence of a sulfuric acid or benzene sulfonic acid catalyst and sufficient sulfolane, alkyl-substituted sulfolane or dialkyl sulfone solvent to provide substantially a one phase reaction mixture, extracting the reaction product with a $C_5$-$C_{20}$ alkane and subsequently recovering the β-(sec-alkoxy) ethanol product from the alkane extract by, for example, distillation.

BRIEF DESCRIPTION OF THE DRAWINGS

FIG. 3 is a set of curves that illustrate enhanced yields for specific concentrations of solvent and acid catalyst for two systems: one using 3-methylsulfolane and one using 2,4-dimethylsulfolane.

DESCRIPTION OF THE PREFERRED EMBODIMENTS

The olefin feed (10) to reactor (1) is typically a substantially linear (greater than 70%) mono-olefin having from about 8 to about 22, preferably from about 11 to about 18 carbon atoms. The olefins are alpha-, or internal and mixtures of both.

That acid catalyst is selected from the group consisting of sulfuric and benzene sulfonic acids. The terms sulfuric and benzene sulfonic acid include the monohydrates, i.e. $H_2SO_4.H_2O$ and $C_6H_5SO_3H.H_2O$. The optimum concentration of acid used will depend on the particular solvent used. FIG. 3 shows the benzene sulfonic acid concentration [(H+)M] for 3-methylsulfolane and 2,4-dimethylsulfolane solvents. In general, the acid concentration appears to range from about 0.2 to about 1.8. Typically, more benzene sulfonic acid than sulfuric acid was needed to achieve a given conversion.

The reactant solvent is selected from the group consisting of sulfolane (tetrahydrothiophene 1,1 dioxide), alkyl-substituted sulfolanes, dialkyl sulfones and mixtures thereof where the alkyl group or groups contain from 1 to about three carbon atoms. Illustrative of the alkyl-substituted solfolanes and sulfones are 2-methylsulfolane, 3-methylsulfolane, 2,4-dimethyl-sulfolane, 3,4-dimethyl sulfolane, dimethylsulfone, diethylsulfone, diisopropylsulfone. There are optimum ratios of reactant solvent to olefin depending upon which solvent is used. FIG. 3 shows the effect of reactant solvent concentration on yield for two different solvents: 3-methylsulfolane and 2,4-dimethylsulfolane. Below olefin: 3-methylsulfolane molar ratios of 1:13, the reaction mixture was two phase and conversion dropped. The same phenomenon is seen in the 2,4-dimethylsulfolane case except the optimum ratio is about 1:7. These optima can be determined for each solvent by routine experimention.

In general, reaction temperatures range from about 80° to about 180° C., preferably 100°–150° C., and most preferably 120° C.–140° C. and pressures range from about 1 atm to about 100 atm, although pressures are not critical.

The paraffinic type of solvent utilized in the instant process to extract the product β-(sec-alkoxy) ethanol and unreacted olefin from the reaction stream is an alkane having a carbon number ranging from about 5 to about 20 carbon atoms.

Figure 1:
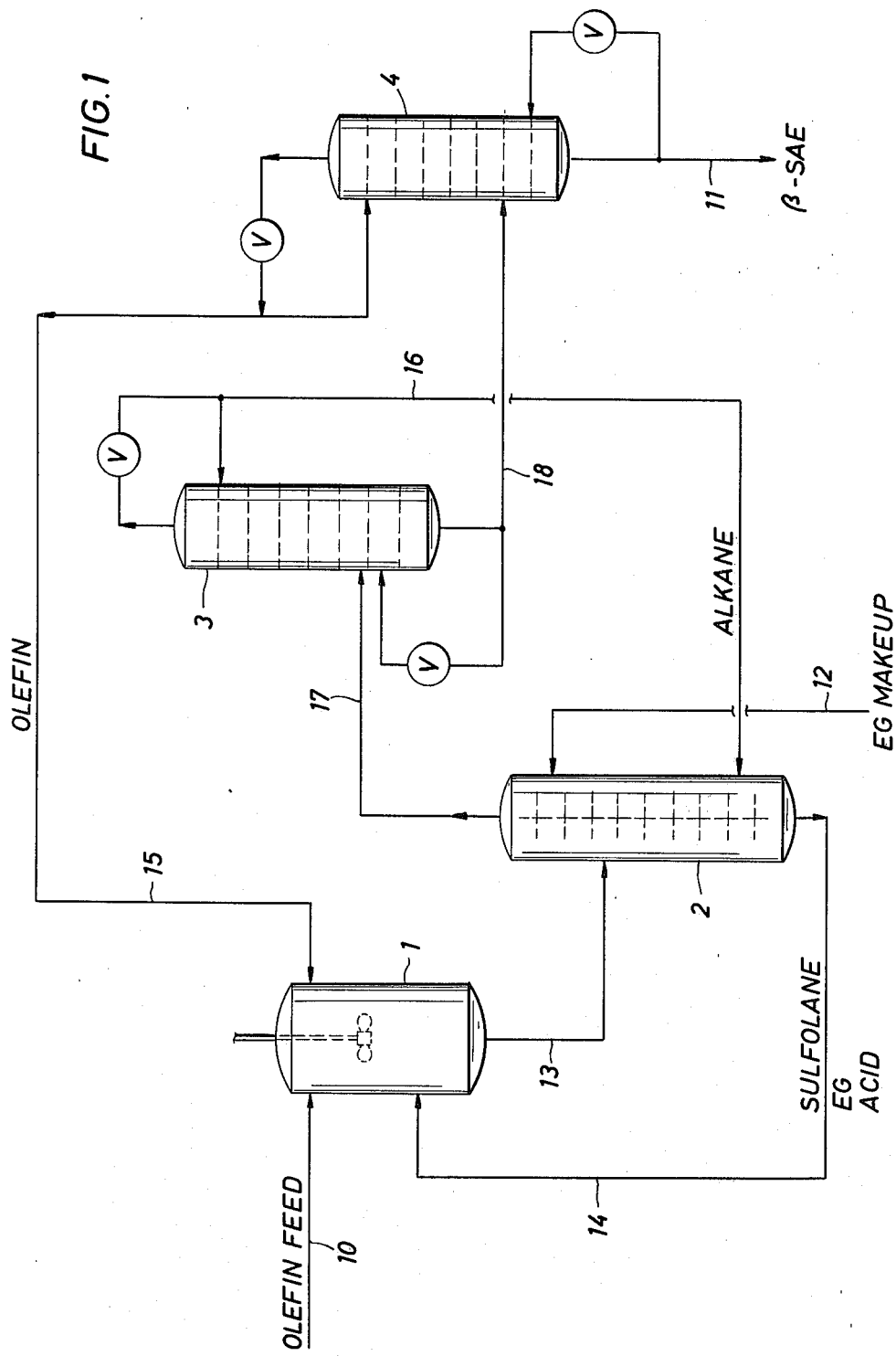
FIG. 1 is an illustrative embodiment in schematic form of the instant invention utilizing sulfolane as a solvent.

FIG. 1 is a simplified flow scheme which illustrates the invention's basic steps of reaction, extraction and recovery of product. This embodiment is particularly suitable when sulfolane is utilized as a reaction solvent. Other variations will occur to one skilled in the art. The reaction is carried out in a heated, stirred reactor (1). The reaction product is removed from the reactor and fed through line 13 to the hydrocarbon extractor (2). In this case, the hydrocarbon extractor (2) is operating as a two solvent extractor. The product is fed to an intermediate stage of the extractor. The extractant alkane is fed to a lower stage and removes unreacted olefin and β-(sec-alkoxy) ethanol as it moves up through the reactor leaving a raffinate phase containing sulfolane, ethylene glycol and catalyst to be recycled to the reactor (via line 14). Make-up ethylene glycol is fed into the top of the reactor by line 12 and strips traces of acid catalyst and sulfolane from the extract stream. The extract stream is then feed (via line 17) to a hydrocarbon flasher (3) where the extractant alkane is stripped off and recycled to the hydrocarbon extractor (2) (via line 16). The bottoms stream from the flasher (3) containing primarily unreacted olefin and β-(sec-alkoxy) ethanol is fed via line 18 to a distillation column (4) wherein it is separated into an overhead stream (15) containing primarily unreacted olefin which is recycled to the reactor (1) and a stream which contains primarily the product β-(sec-alkoxy) ethanol.

EXPERIMENTS

To test out various solvents and catalysts, a 100-ml stirred, glass vessel heated to 130° C. was utilized. The reaction was charged in the following order: glycol, 1,4-dimethyl sulfolane acid and olefin and heated at 130° C. for 13 hours. The olefin was mixed internal $C_{11}$ and $C_{12}$ olefin about 50–50 molar ratio): For this scouting reaction, the olefin/β-(sec-alkoxy) ethanol layer was isolated by separatory funnel after copious quantities of water had been added to the reaction solution. The results are shown in Table 1. Yields of the β-(sec-alkoxy) ethanol were optimized for various ratios of reactant solvents (3-methyl sulfolane and 2,4-dimethyl sulfolane) and for various concentration of benzene sulfonic acid. These results are plotted in FIG. 3.

TABLE I

YIELDS OBTAINED USING VARIOUS SOLVENTS & CATALYSTS

| Experiment | Conv. m % | Catalyst | Molar ratios $C_n$:EG:Solv:H | Selectivities m % | | | Solvent |
| --- | --- | --- | --- | --- | --- | --- | --- |
| | | | | RR'OH | (EO)$_1$ | (EO)$_2$ | |
| 1 | 14.3 | CF$_3$SO$_3$H.H$_2$O | 1:6:17:0.2 | 5.0 | 86.6 | 8.3 | 3-MeSA |
| 2 | 5.9 | C$_6$H$_5$SO$_3$H.H$_2$O | 1:3:10:0.26 | 5.8 | 94.2 | trace | 3-MeSA |
| 3 | 8.1 | H$_2$SO$_4$.H$_2$O | 1:3:10:0.26 | 7.6 | 92.8 | trace | 3-MeSA |
| 4 | 15.3 | CF$_3$SO$_3$H.H$_2$O | 1:4:13.3:0.17 | 6.9 | 83.6 | 9.5 | 3-MeSA |
| 5 | 12.3 | H$_2$SO$_4$.H$_2$O | 1:5:5.4:0.22 | 4.2 | 91.6 | 4.2 | isopropylsulfone |
| 6 | 12.2 | C$_6$H$_5$SO$_3$H.H$_2$O | 1:5:5.5:0.22 | 5.3 | 92.1 | 2.6 | isopropylsulfone |
| 7 | 16.5 | H$_2$SO$_4$.H$_2$O | 1:5:7:0.24 | 10.2 | 93.0 | 6.8 | DMSA |
| 8 | 15.0 | C$_6$H$_5$SO$_3$H.H$_2$O | 1:5:7:0.48 | 5.0 | 93.0 | 1.9 | DMSA |
| 9 | 14.6 | CF$_3$SO$_3$H.H$_2$O | 1:4:6:0.10 | 8.0 | 78.5 | 13.5 | DMSA |
| 10 | 12.7 | H$_2$SO$_4$.H$_2$O | 1:4:6:0.20 | 3.7 | 89.0 | 7.3 | DMSA |
| 11 | 12.3 | C$_6$H$_5$SO$_3$H.H$_2$O | 1:4:6:0.20 | 2.5 | 94.9 | 2.5 | DMSA |

*(EO)$_1$ = RR'CHOCH$_2$CH$_2$OH
(EO)$_2$ = RR'CHOCH$_2$CH$_2$OCH$_2$CH$_2$OH
RR'OH = internal alcohol (RR' here and above are not the same)

bottoms product stream (11) containing substantially the desired product, β-(sec-alkoxy) ethanol.

Figure 2:
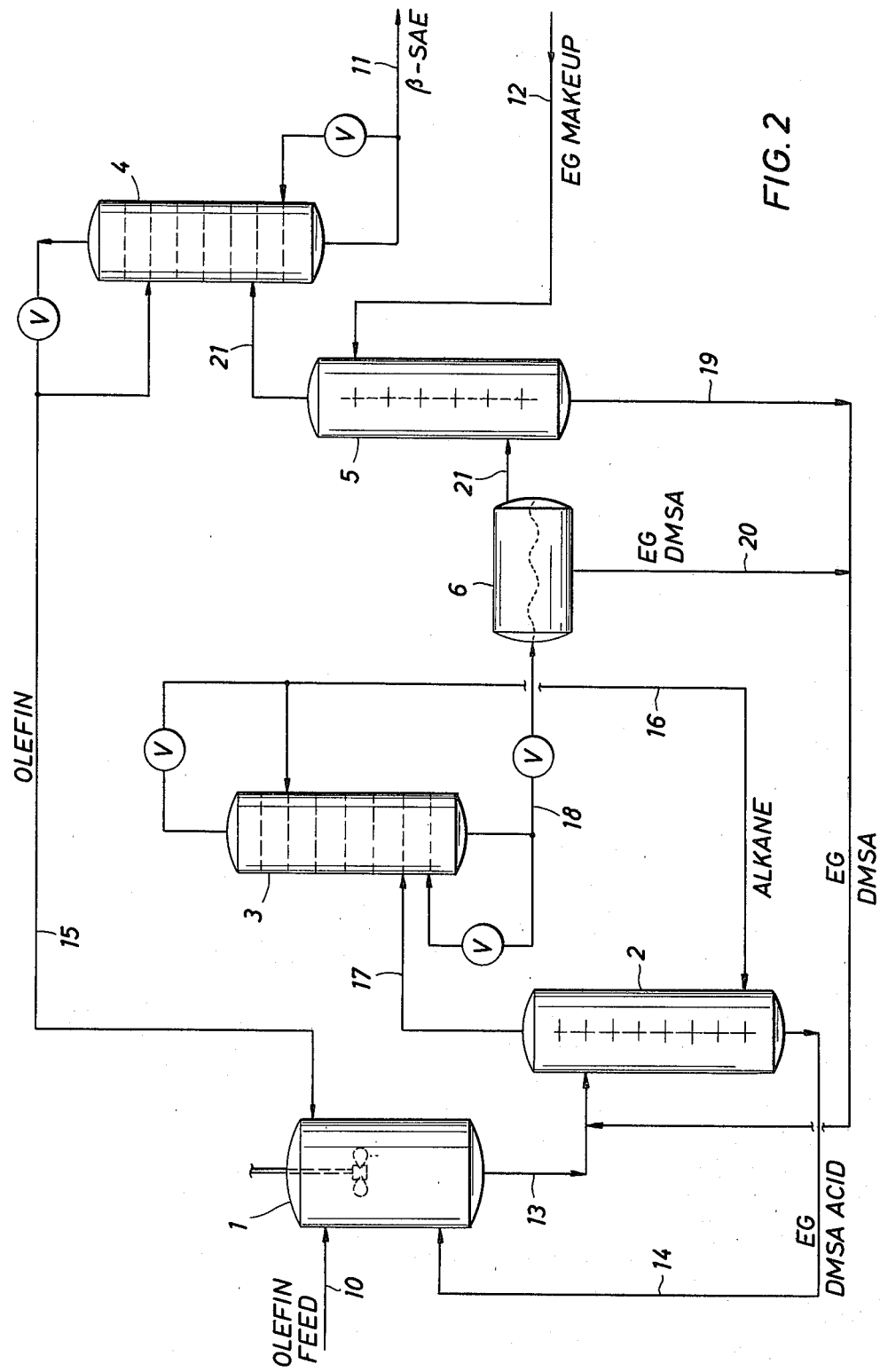
FIG. 2 is an illustrative embodiment in schematic form of the instant invention utilizing 2,4-dimethylsulfolane as a solvent.

FIG. 2 illustrates another alternative embodiment of the instant invention. This embodiment is preferred for these reactant solvents such as dimethylsulfolane having decreased polarity compared to sulfolane. The reaction is carried out in a heated, stirred reactor (1). The reaction product is removed from the reactor and fed through line 13 to the hydrocarbon extractor (2). In this case, the hydrocarbon extractor (2) is a single solvent extractor and operated at the reaction temperature. The bottoms stream (14) from the reactor containing ethylene glycol, dimethyl sulfolane and acid catalyst is recycled to the reactor (1). The extract phase is routed (via 17) to a hydrocarbon flasher (3) which strips off the extractant alkane and returns it (via 16) to the extractor (2). The bottoms stream (18) is cooled and routed to a phase separator (6) and separated into a polar phase (20) containing primarily dimethyl sulfolane and ethylene glycol which is recycled to the extractor (2) (or alternately to the reactor (1)) and a non-polar phase (21) containing primarily unreacted olefin and β-(sec-alkoxy) ethanol which is routed (via 21) to a second extractor (5). Makeup ethylene glycol (12) is fed to the top of the extractor (5) which strips trace amounts of acid catalyst and dimethyl sulfolane from the product containing stream. The ethylene glycol and the stripped materials are rerouted (via 19) to the hydrocarbon extractor (2) (or alternatively to the reactor (1)). The product containing stream is sent (via 21) to a distillation column where it is separated into an overhead stream (15) containing primarily unreacted olefin which is recycled back to the reactor (1) and a bottom product To test out the instant invention concept of reaction and extraction followed by purification, larger (1000–2000 ml) stirred glass vessels were utilized. The vessels were charged in the following order: glycol, solvent, acid and olefin. The reactor was heated at 130° C. for 3 hours. The reaction mixture was cooled to room temperature and then extracted with pentane in a 5-stage cross current extraction. (separatory funnel) using 400 ml of pentane per stage. The pentane washings (extraction phase) were combined and the pentane removed by rotary evaporation after a water washing (3× = 1000 ml) which removed traces of ethylene glycol and 1,2-dimethylsulfolane. The lower layer containing ethylene glycol, 1,4-dimethyl sulfolane and acid was sparged with N$_2$ to remove the traces of pentane before recycling. Make up ethylene glycol was also added. The unreacted olefin and β-(sec-alkoxy) ethanol were separated by vacuum distillation in a 5-tray Oldershaw column (olefin boiling point 98°–108° C. at 26 torr, and product β-(sec-alkoxy) ethanol boiling point ~140 at 500μ). The results are shown in Table II. In the experiment, the olefin/β-(sec-alkoxy) ethanol extraction was simplified necessarily to avoid working with hot solvents and exotic equipment. In lieu of a cross-current extractor, a countercurrent extractor would be used commercially. The extraction was performed at room temperature, but since the extraction coefficients of β-(sec-alkoxy) ethanol at room temperature and 130° C. are virtually identical, little variations in the β-(sec-alkoxy) ethanol would be expected at room temperature versus the reaction temperature of 130° C. Although the experiments were batch, they also demonstrate the feasibility of recycling the ethylene glycol/dimethyl sulfolane/acid phase and the unreacted olefin.

TABLE II $C_{11}/C_{12}$ + EG→β-SAE ($EO_1$, $EO_2$, $EO_3$) + RR'OH + ...[d]

130° C.
3 hrs
DMSA Solvent 1:5:7.5
173-gm $C_n$ = Scale $C_n$:EG:Solvent m Ratios

| Experiment | Conv[a] (m %) | Selectivities (m %) | | | | | Recycle[b] Numbers | Material Balance (w %) | H⁺ Conc[c] (equiv/gm) | Remarks |
|---|---|---|---|---|---|---|---|---|---|---|
| | | RR'OH | $EO_1$ | $EO_2$ | $EO_3$ | $EO_4$ | | | | |
| $C_6H_5SO_3H.H_2O$ Catalyst 0.417 in EG/DMSA phase] | | | | | | | | | | |
| 12 | 15.3 | 5.9 | 91.5 | 2.6 | — | — | 0 | 92.4 | 0.30 | Virgin i-$C_{11}/C_{12}$ olefin |
| 13 | 14.4 | 5.9 | 89.1 | 5.0 | — | — | 1 | 93.9 | 0.31 | Virgin i-$C_{11}/C_{12}$ olefin |
| 14 | 14.9 | 7.3 | 85.7 | 7.1 | — | — | 2 | 92.6 | 0.32 | Virgin i-$C_{11}/C_{12}$ olefin |
| 15 | 14.4 | 7.9 | 82.7 | 8.8 | 0.6 | — | 2 | 92.4 | 0.31 | Virgin i-$C_{11}/C_{12}$ olefin |
| 16 | 12.3 | 7.1 | 80.7 | 10.3 | 1.4 | 0.5 | 4 | 80.0 | 0.32 | Virgin i-$C_{11}/C_{12}$ olefin |
| 17 | 13.0 | 7.1 | 79.8 | 12.9 | 1.0 | 1.0 | 5 | 95.4 | 0.32 | Virgin i-$C_{11}/C_{12}$ olefin |
| 18 | 15.6 | 4.6 | 92.7 | 2.6 | — | — | 0 | 96.9 | 0.28 | Recycle olefin |
| 19 | 14.5 | 5.3 | 89.5 | 5.2 | — | — | 1 | — | 0.31 | Recycle olefin |
| 20 | 13.7 | 4.2 | 86.9 | 8.8 | — | — | 2 | 96.6 | 0.32 | Recycle olefin |
| 21 | 13.6 | 5.3 | 81.7 | 11.0 | 0.4 | 1.6 | 3 | 97.2 | 0.32 | Recycle olefin |
| $H_2SO_4.H_2O$ Catalyst 0.217 in EG/DMSA phase] | | | | | | | | | | |
| 22 | 17.4 | 6.9 | 88.3 | 4.8 | — | — | 0 | 99.2 | 0.19 | Virgin i-$C_{11}/C_{12}$ olefin |
| 23 | 13.2 | 3.9 | 89.2 | 6.9 | — | — | 1 | 98.9 | 0.16 | Virgin i-$C_{11}/C_{12}$ olefin |
| 24 | 12.6 | 6.7 | 80.9 | 11.2 | 1.1 | trace | 2 | 98.3 | 0.13 | Virgin i-$C_{11}/C_{12}$ olefin |
| 25 | 11.4 | 8.7 | 78.0 | 11.6 | 1.7 | trace | 3 | 97.3 | 0.15 | Virgin i-$C_{11}/C_{12}$ olefin |
| 26 | 16.5 | 4.0 | 89.5 | 6.5 | — | — | 0 | 99.2 | 0.21 | Recycle olefin |
| 27 | 14.5 | 4.5 | 84.9 | 10.2 | 0.5 | trace | 1 | 99.3 | 0.19 | Recycle olefin |
| 28 | 13.5 | 5.1 | 76.2 | 15.1 | 1.5 | 2.1 | 2 | — | 0.19 | Recycle olefin |

[a] Conversion based on extracted material
[b] Recycle number refers to the number of times the EG/DMSA/H⁺ phase was recycled.
[c] Initial reaction n = 0.
[d] Concentration value reported after reaction completed.
β-SAE ($EO_1$) = RR'CHOCH$_2$CH$_2$OH
β-SAE ($EO_2$) = RR'CHOCH$_2$CH$_2$OCH$_2$CH$_2$OH
β-SAE ($EO_3$) = RR'CHOCH$_2$CH$_2$OCH$_2$CH$_2$OCH$_2$CH$_2$OH
RR'OH - internal alcohol (R' here and above are not the same).

What is claimed is:

1. A process for preparing β-(sec-alkoxy) ethanol which comprises (a) reacting an olefin having from about 8 to about 22 carbon atoms with ethylene glycol at a temperature ranging from about 80° to about 180° in the presence of an acid catalyst selected from the group consisting of sulfuric acid and benzenesulfonic acid and sufficient solvent to provide a one phase reaction medium with the solvent consisting essentially of a substance selected from the group consisting of, 2,4-dimethylsulfolane, 3,4-dimethylsulfolane, and mixtures thereof, (b) extracting the reaction product with an alkane having a carbon number ranging from about 5 to about 20 and (c) recovering the β-(sec-alkoxy) ethanol product from the alkane product.

2. The process of claim 1 wherein the solvent is 2,4-dimethylsulfolane.

* * * * *